(12) United States Patent
Wabel

(10) Patent No.: US 12,337,091 B2
(45) Date of Patent: Jun. 24, 2025

(54) APPARATUS AND METHOD FOR PREPARING A PERITONEAL DIALYSIS SOLUTION

(71) Applicant: Fresenius Medical Care Deutschland GmbH, Bad Homburg (DE)

(72) Inventor: Peter Wabel, Darmstadt (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 774 days.

(21) Appl. No.: 16/617,532

(22) PCT Filed: May 30, 2018

(86) PCT No.: PCT/EP2018/064134
§ 371 (c)(1),
(2) Date: Nov. 27, 2019

(87) PCT Pub. No.: WO2018/219981
PCT Pub. Date: Dec. 6, 2018

(65) Prior Publication Data
US 2020/0179584 A1 Jun. 11, 2020

(30) Foreign Application Priority Data
May 30, 2017 (DE) ...................... 10 2017 111 803.9

(51) Int. Cl.
*A61M 1/28* (2006.01)

(52) U.S. Cl.
CPC ......... *A61M 1/287* (2013.01); *A61M 2205/15* (2013.01); *A61M 2205/3393* (2013.01);
(Continued)

(58) Field of Classification Search
CPC .............. A61M 1/287; A61M 2205/15; A61M 2205/3393; A61M 2205/36; A61M 2205/502; A61M 2205/702
See application file for complete search history.

(56) References Cited

U.S. PATENT DOCUMENTS 4,585,436 A 4/1986 Davis et al.
4,898,578 A * 2/1990 Rubalcaba, Jr. ...... A61M 5/172
700/83
(Continued)

FOREIGN PATENT DOCUMENTS

EP 0 619 135 4/1994
GB 2135598 A * 9/1984 ............... A61B 5/16
(Continued)

*Primary Examiner* — Rebecca E Eisenberg
*Assistant Examiner* — Nhu Q. Tran
(74) *Attorney, Agent, or Firm* — Kilyk & Bowersox, P.L.L.C.

(57) ABSTRACT

The invention relates to an apparatus for preparing a peritoneal dialysis solution at the point of use comprising a disposable having a solution bag and associated filling lines and patient lines; a storage unit for liquid connected to the filling line; a control unit; and actuators for regulating a flow from the storage unit to the disposable, wherein the apparatus furthermore comprises a scale at which the solution bag of the disposable is arranged, with the control unit being configured to initiate a filling of the solution bag with liquid from the storage unit using the actuators and to determine the quantity of the liquid that has flowed into the solution bag using the scale.

11 Claims, 10 Drawing Sheets

Figure 1:
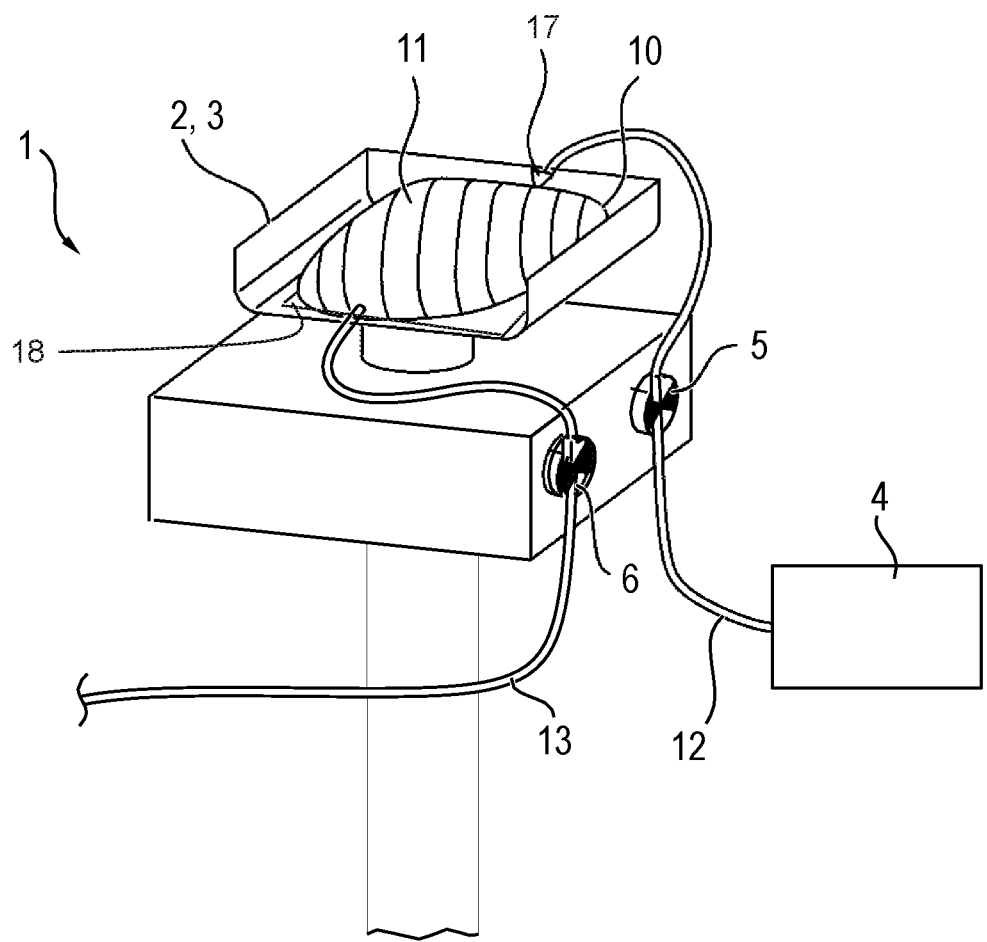

(52) U.S. Cl.
CPC ... *A61M 2205/36* (2013.01); *A61M 2205/502* (2013.01); *A61M 2205/702* (2013.01); *A61M 2209/08* (2013.01)

(56) References Cited

U.S. PATENT DOCUMENTS

| | | | | |
|---|---|---|---|---|
| 5,722,947 | A * | 3/1998 | Jeppsson | A61M 1/28 128/DIG. 13 |
| 8,226,595 | B2 * | 7/2012 | Childers | A61M 1/288 604/119 |
| 2003/0217972 | A1 * | 11/2003 | Connell | G06F 3/04847 210/94 |
| 2003/0225066 | A1 * | 12/2003 | Polaschegg | A61K 31/19 514/557 |
| 2019/0307939 | A1 * | 10/2019 | Lo | A61M 1/28 |

FOREIGN PATENT DOCUMENTS

| | | |
|---|---|---|
| WO | WO 95/20985 | 8/1995 |
| WO | WO 2016/087043 | 6/2016 |

* cited by examiner

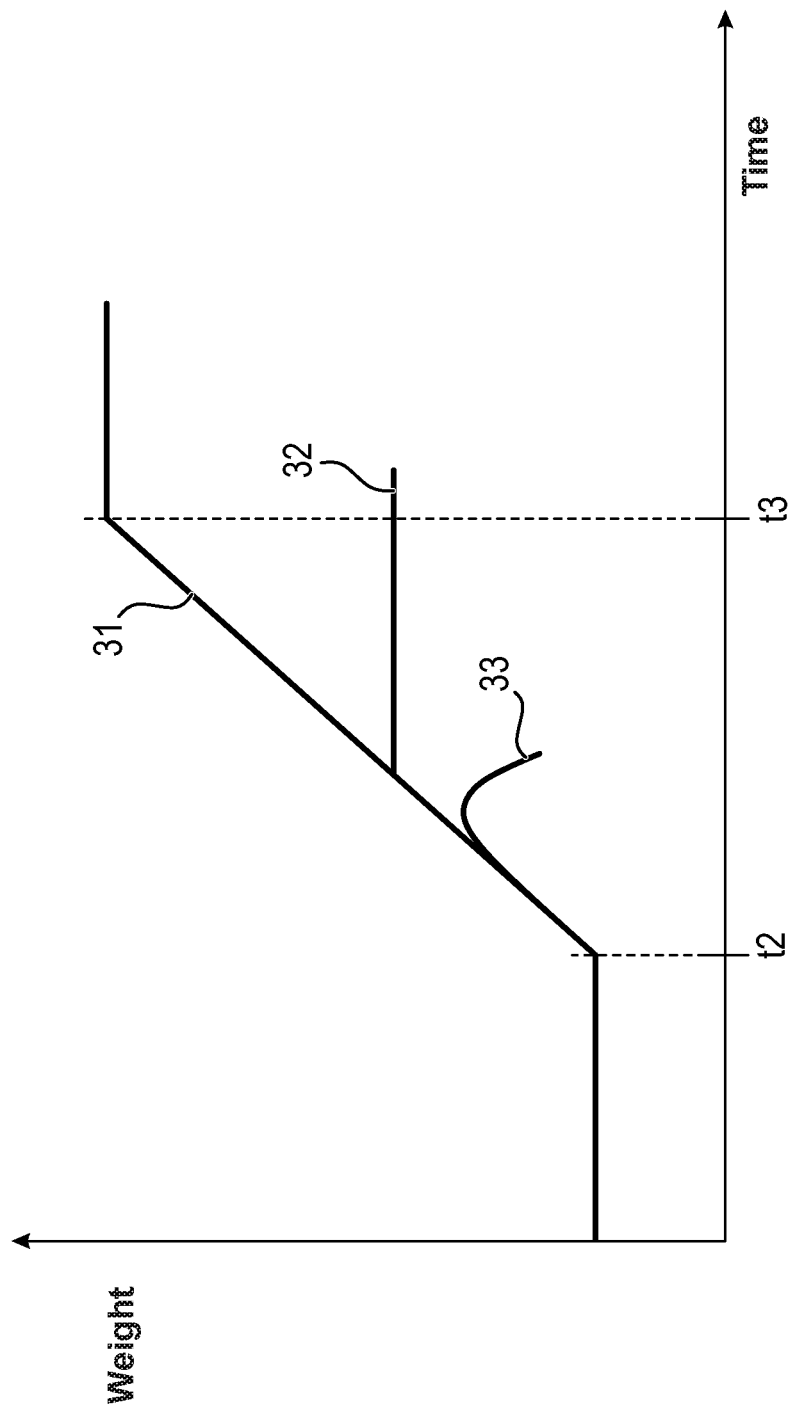

APPARATUS AND METHOD FOR PREPARING A PERITONEAL DIALYSIS SOLUTION

The invention relates to an apparatus for the carrying out of a point-of-care peritoneal dialysis treatment and to a method for the preparation of a peritoneal dialysis solution at the point of use.

Peritoneal dialysis is also abbreviated to PD. There are various PD processes, including the processes of automated peritoneal dialysis (APD) carried out using peritoneal dialysis machines. In this process, the machine supplies a dialysis solution into the abdomen of the patient via a catheter in the introduction phase.

The inflow of the dialysis solution to the patient and/or the drainage of consumed dialysis solution from the patient can take place by means of one or more pumps and/or gravimetrically, i.e. by the force of gravity. Both variants and also a combination thereof are generally covered by the invention.

The dialysis solution is then left in the abdominal cavity during a dwell period. In this respect, low-molecular substances can pass from the blood via the capillary vessels of the peritoneum into the dialysis solution since a concentration gradient is present. Water can furthermore be removed from the body in this manner provided that the dialysis solution has a higher content of osmotically active substances than the blood. After the end of the dwell period, the machine removes the dialysis solution enriched with eliminated substances and consequently used up in a drainage phase from the abdominal cavity again via the catheter.

In a so-called point of care peritoneal dialysis (PoC PD), the dialysis solution is prepared at the point of use, for example directly at the patient's home. The dilution of a concentrate or a different type of mixture of different starting components can be provided for this purpose, for example. The solution prepared on site is provided to the patient or is applied directly by the peritoneal dialysis machine.

It is the object of the invention to provide a solution with which a particularly simple preparation of a peritoneal dialysis solution insusceptible to error is made possible at the point of use and a carrying out of a point-of-care peritoneal dialysis is made possible.

Against this background, the invention relates to an apparatus for preparing a peritoneal dialysis solution at the point of use comprising a disposable having one or more solution bags and associated filling lines and patient lines, a storage unit for liquid connected to the filling line, a control unit and actuators for regulating a flow from the storage unit to the disposable. Provision is made in accordance with the invention that the apparatus furthermore comprises a scale at which the solution bag of the disposable is arranged, with the control unit being configured to initiate a filling of the solution bag with liquid from the storage unit using the actuators and to determine the quantity of the liquid that has flowed into the solution bag using the scale. The scale can have a support surface and in particular a support tray or a suspension apparatus for the bag.

The solution bag or bags can lie on the scale, can be suspended thereat, etc. It is also conceivable that the scale has slots in which one or more solution bags are received.

It is pointed out at this point that the term "a" and "one" does not necessarily relate to exactly one of the elements in question, although this is a conceivable embodiment, but also comprises a plurality thereof. The use of the singular of an element equally also comprises its plurality and vice versa.

It is furthermore pointed out that the term "solution bag" stands in general and as a representative for any desired container that contains the solution or in which the solution can be received. It can in this respect be a container, a bag in the narrower sense or any other receptacle having rigid and/or flexible walls.

Provision is made in an embodiment that the apparatus comprises a pump and that the control unit is configured to initiate an active conveying of the liquid to the solution bag. Provision can be made that the pump is a balancing pump with which the liquid volume conveyed to the solution bag can be determined.

Provision is made in an embodiment that the apparatus comprises a flow regulator and that the control unit is configured to initiate a gravimetric flow of the liquid into the solution bag using the flow regulator. The flow regulator can, for example, be a valve or a clamp.

Provision is made in an embodiment that the control unit is configured to control the liquid quantity filled into the solution bag using a balancing pump or to regulate it on the basis of the signal of a flow sensor and only to make use of the signal of the scale to check the quantity of liquid filled into the solution bag. Alternatively or additionally to a balancing pump, a flow sensor can also be provided to determine the quantity of liquid flowing into the bag.

Provision is made in an embodiment that the control unit is configured to regulate the quantity of liquid filled into the solution bag using the signal of the scale. Provision can therefore be made that the signal of the scale is used by the control unit to regulate the flow to the solution bag. In this embodiment, a balancing pump and a flow sensor can be dispensed with.

Provision is made in an embodiment that the solution bag is pre-filled with a dialysis fluid concentrate, that the storage unit is a water preparation unit, and that the liquid filled into the solution bag is water. When filling with water, the concentrate is diluted to prepare the dialysis solution. The dialysis liquid solution can be a solid concentrate or a liquid concentrate. The solution bag can, for example, contain a liquid solution concentrate that has to be diluted before use with, for example, 10 to 20 times the amount of sterile water to obtain a dialysis solution ready to use. An exactly defined quantity of sterile water therefore has to be supplied to a defined quantity of concentrate to obtain a dialysis solution ready to use having the components in the correct concentrations. The bag can comprise means for retaining the concentrate, for example separable weld seams or the like.

The solution bag can comprise one or more compartments. In the case of a plurality of compartments, they can, for example, be separated from one another by weld seams. The volume of the solution bag is large enough to receive the quantity of dialysis liquid required for a treatment cycle.

Provision can furthermore be made that a heating 18 (FIG. 1) is located beneath the solution bag or bags (e.g. disposable bags).

Provision is made in an embodiment that the storage unit is configured to store at least two different fluid solution components and that the control unit is configured to initiate a sequential filling of the solution bag with the different solution components. The fluid solution components can be pure water or concentrated partial solutions and/or diluted partial solutions. Suitable partial solutions, for example, comprise a glucose solution or an electrolyte solution. The solution bag can, for example be sequentially filled with water, with a glucose solution, and with an electrolyte solution in three steps. A plurality of repetitions of a sequence of steps can also be provided, that is, for example, a first step in which the solution bag is filled with a specific quantity of a first partial solution, followed by a second step in which the solution bag is filled with a specific quantity of a second partial solution, followed by a third step in which the solution bag is in turn filled with a specific quantity of the first partial solution, and so on. The solution bag can be empty before filling in this embodiment; however, a pre-filling with a concentrate can alternatively also be provided here.

Provision is made in an embodiment that the storage unit comprises a reverse osmosis filter to produce sterile and pure water.

Provision is made in an embodiment that the control unit is configured to output a signal and/or to suppress a start of the filling procedure or to adapt the filling procedure when the starting weight of the bag determined using the scale falls below or exceeds a threshold value. A desired value is stored in the control unit for the weight of the empty solution bag or of the solution bag filled with concentrate or is transmitted to it or is located at the solution bag, e.g. in the form of a barcode, and is read by the control unit. The control unit can therefore determine the weight of the solution bag before the start of the filling procedure using the scale and can thus verify whether a bag having the correct weight has been placed in correctly or whether the bag has lost liquid due to a leak or to incorrect storage. The desired range can correspond to a desired value stored in the control unit including a tolerance range of, for example, 5%, 2% or 1% in either direction. The desired range can also be calculated or be present as an absolute value.

The desired value can result from the prescription. Provision can furthermore be made that the apparatus comprises a reading device and the control unit is configured to read in the desired value. Provision can be made in this connection that the bag weight is already determined in production and that the measured weight is recorded on the bag, for example using a barcode or an RFID chip. The documented weight can then be compared with the weight actually measured at the apparatus before the start of the filling procedure. Differences can be an indication of an incorrect storage or of damage.

Provision is made in an embodiment that the control unit is configured to start the filling procedure after a user input.

Provision is made in an embodiment that the control unit is configured to stop the filling procedure after reaching a predefined filling quantity and to verify by means of the scale whether the weight of the bag is within a desired range after the stopping of the filling procedure. The stopping of the filling procedure takes place, for example, by a stopping of the pump or by the flow regulator, for example by the closing of a clamp or by an indication to the user who then stops the flow. The stopping of the filling procedure can be a final stop at the end of the total filling procedure or an intermediate stop according to a step of a multi-stage filling procedure in which the solution bag is filled with different solution components in sequential steps. The control unit can therefore determine the weight of the solution bag using the scale after the filling procedure or after the respective step of the filling procedure and can thus verify whether a correct liquid quantity has flowed into the solution bag within the framework of the filling procedure or of the preceding step. The desired range can correspond to a desired value stored in the control unit including a tolerance range of, for example, 5%, 2% or 1% in either direction. Absolute values are also conceivable as tolerance ranges in this respect and are also covered by the invention.

The desired value is preferably stored in the control unit and can result from the prescription.

The control unit can therefore determine the weight of the solution bag using the scale before the filling procedure, after any intermediate stop of the filling procedure, and after the end of the filling procedure and can thus verify whether a correct liquid quantity has flowed into the solution bag.

Provision is made in an embodiment that the control unit is configured to fix the limits of the desired range by addition of a specific amount to the determined starting weight of the bag or to a weight of the bag determined after the preceding step. The desired value and the limits of the desired range are thus not fixedly predefined as absolute numbers, but only as a difference amount from the weight of the empty bag or of the partially filled bag. If absolute numbers were fixed, there would be the risk that when the weight of the empty weight does not, for example, correspond exactly to the theoretical desired value, but differs therefrom within the tolerance range, the weight verification of the next step would be falsified by the amount of the deviation. This problem is avoided by the referencing to the actually determined weight.

It is also possible that on a step-wise filling, a filling volume that may be too large/too little can or must be corrected in one of the subsequent steps.

Provision is made in an embodiment that the control unit is configured to output a signal after the end of the filling procedure to request a movement of the filled solution bag and to verify by means of the scale whether the solution bag has actually been moved. The user can thus be caused to move the solution bag for the homogeneous mixing of the solution components after its complete filling. The user can, for example, remove the bag from the scale, in particular from the support surface or from the suspension apparatus and can place it back on the scale or he can move it on the scale. The movement can be verified using the scale in that a disturbance and a subsequent readopting of the end weight of the bag can be recognized.

A weld seam that separates different solution parts from one another before being opened can also be opened for the purpose of mixing.

Provision is made in an embodiment that the apparatus has an actuator that is configured to be able to move the inserted solution bag and that the control unit is configured to move the solution bag after the end of the filling procedure. A motor can, for example, be provided that causes a vibration of the support surface or of the suspension apparatus of the scale. A homogeneous mixing can thus be achieved without the user having to remove the solution bag.

Provision is made in an embodiment that the control unit is configured to output a signal and/or to stop the pump of the storage unit and/or to close the filling clamp if a stagnation of the weight increase or a weight reduction of the solution bag is recognized with reference to the scale during the filling procedure. An unwanted backflow of dialysis solution into the water preparation unit can be prevented by a closing of the filling clamp.

Provision is made in an embodiment that the apparatus has a heating and that the control unit is configured to heat the bag during the filling procedure or after the filling procedure.

Provision is made in an embodiment that a check valve 17 (FIG. 1) is provided in the filling line that suppresses a flow from the bag to the water preparation unit. The check valve is therefore arranged in the disposable in this embodiment. In the event of an error during the filling procedure, a backflow of dialysis solution into the filling unit can thus be prevented or a prevention measure at the machine side can be supported.

The filling line can be located at the same side or at the other side of the solution bag than the patient line. An embodiment is preferred in which the lines are located at oppositely disposed sides.

Provision is made in an embodiment that the apparatus in accordance with the invention is a dialysis machine, preferably a machine for carrying out an automatic peritoneal dialysis as part of a point-of-care dialysis treatment. Provision can be made in this respect that the control unit is configured to start a dialysis treatment automatically after the end of the filling procedure. Provision can alternatively be made that the control unit is configured to release a switch or a field on a touch screen of the user interface after a successful filling, with a dialysis treatment being able to be started manually thereby. An indication signal is also conceivable for the user to start the treatment.

The release can also be the release of the patient clamp.

Provision is made in an embodiment that the apparatus has a filling clamp and a patient clamp, wherein the filling line of the disposable is inserted into the filling clamp and the patient line is inserted into the patient clamp, and wherein the control unit is configured to carry out the filling of the solution bag with an open filling clamp and a closed patient clamp.

Provision is made in an embodiment that the apparatus has a further disposable or that the disposable has an additional cavity for dialyzate flowing out of the patient, said disposable or cavity being arranged on the same scale as the solution bag, with the control unit being configured to gravimetrically determine the quantity of the dialyzate flowing off from the patient as part of a dialysis treatment. The quantity of the dialyzate flowing off can thus also be gravimetrically monitored.

The dialyzate flowing off can also be pumped into the bag by means of a pump.

Provision is made in an embodiment that the apparatus has a graphical user interface preferably having a touch screen and that the control unit is configured to visualize the progression of the filling procedure at the user interface and/or to output signals. Provision can, for example, be made that on a positive conclusion of the determination of the starting weight of the bag and/or on a positive conclusion of the filling procedure, a field appears on the touch screen of the user interface that can be actuated to start the bag filling or to start the dialysis treatment. If the respective test has a negative outcome, a start of the bag filling or of the dialysis treatment is not released and a warning indication and a suitable prompt to take action rather appear on the screen.

Against the initially named background, the invention further relates to a method of preparing a peritoneal dialysis solution at the point of use using an apparatus in accordance with the invention, wherein a filling of the solution bag with liquid from the storage unit is initiated using actuators, and wherein the quantity of the liquid that has flowed into the solution bag is determined using the scale. Advantageous embodiments of the method result from the above description of the configuration of the control unit in the apparatus accordance with the invention. It must be noted that the filling procedure can be carried out without the presence of the patient. A presence of the patient is only necessary during the dialysis treatment taking place after the filling procedure.

The filling can take place automatically or by the carer.

Figure 2:
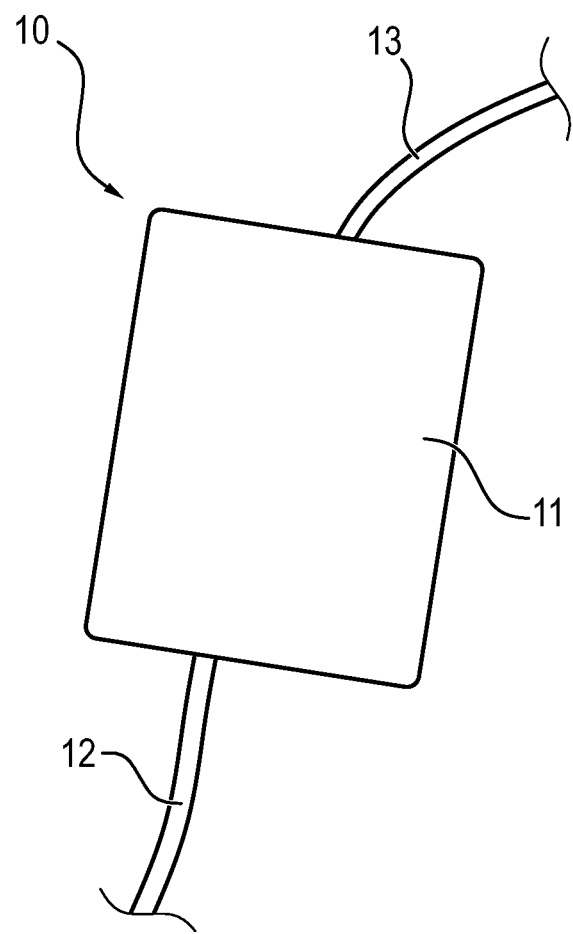
Figure 3:
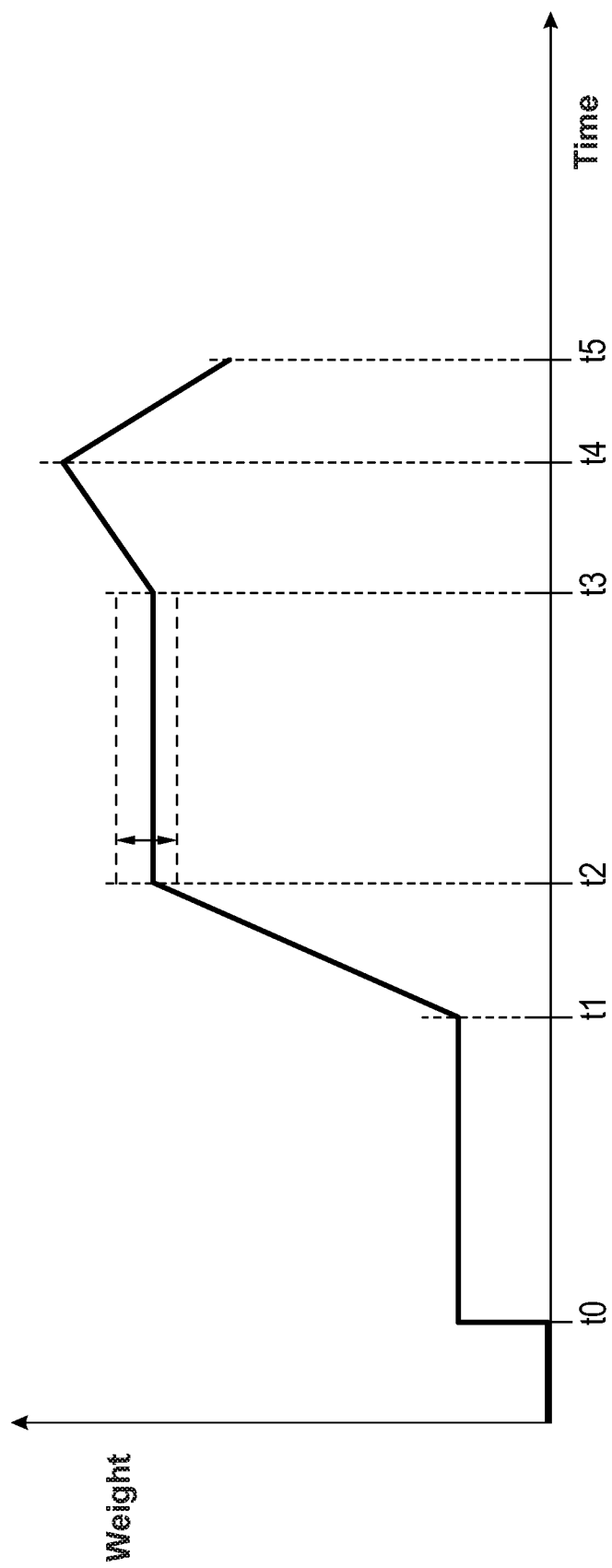
Figure 7:
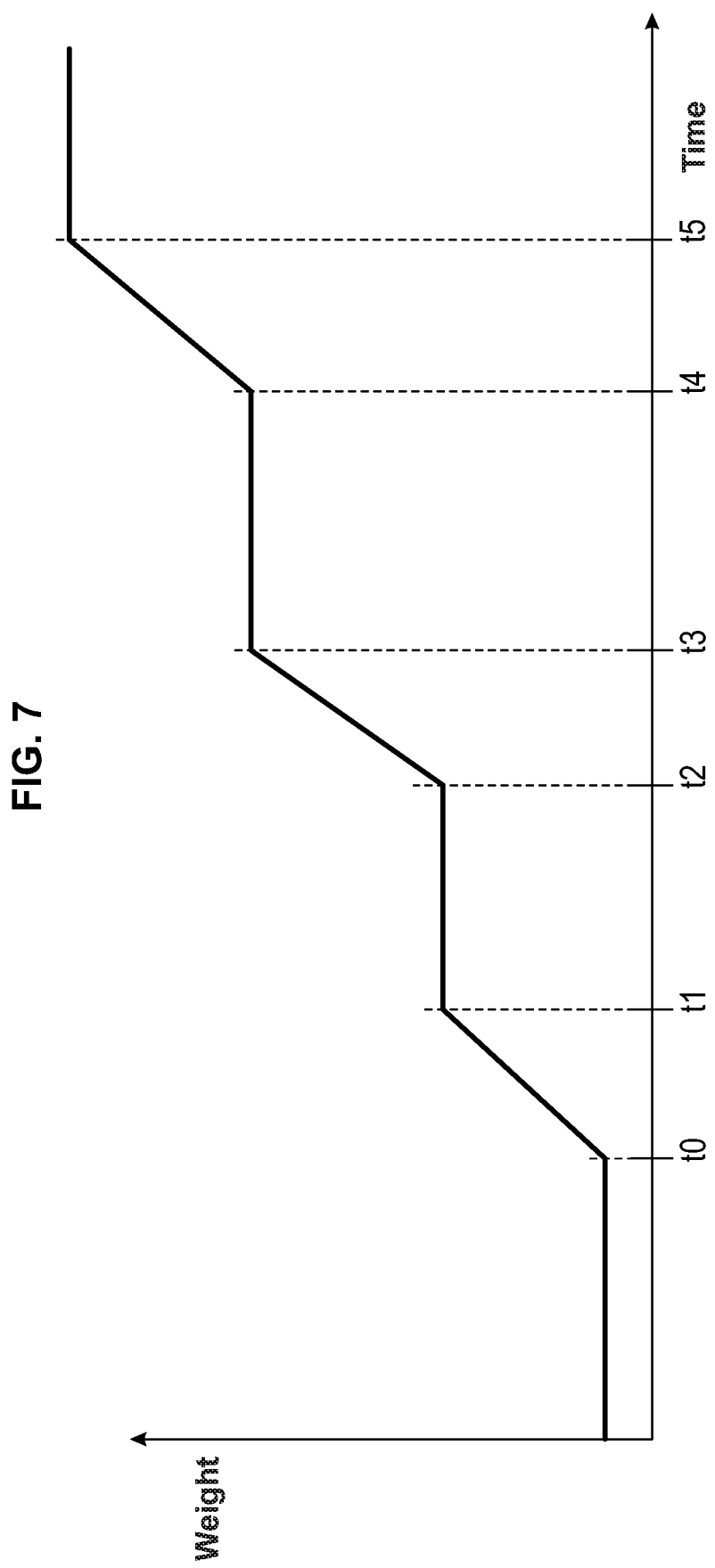

Further details and advantages of the invention result from the embodiment explained in the following with reference to the Figures. There are shown in the Figures:

FIG. 1: a schematic representation of parts of an apparatus in accordance with the invention in a first embodiment;

FIG. 2: a schematic representation of a disposable of the apparatus;

FIG. 3: a history chart of the bag weight measured at the scale of the apparatus;

FIG. 4: a further history chart to illustrate specific disturbances;

FIG. 5: further history charts to illustrate specific partial aspects;

FIG. 6: details of a fluid schematic of a second and third embodiment of an apparatus in accordance with the invention;

FIG. 7: a history chart of the weight measured at the scale of the apparatus in accordance with the second and third embodiments;

FIG. 8: further history charts to illustrate specific partial aspects;

FIG. 9: additional history chart to illustrate yet other part aspects, and

Figure 10:
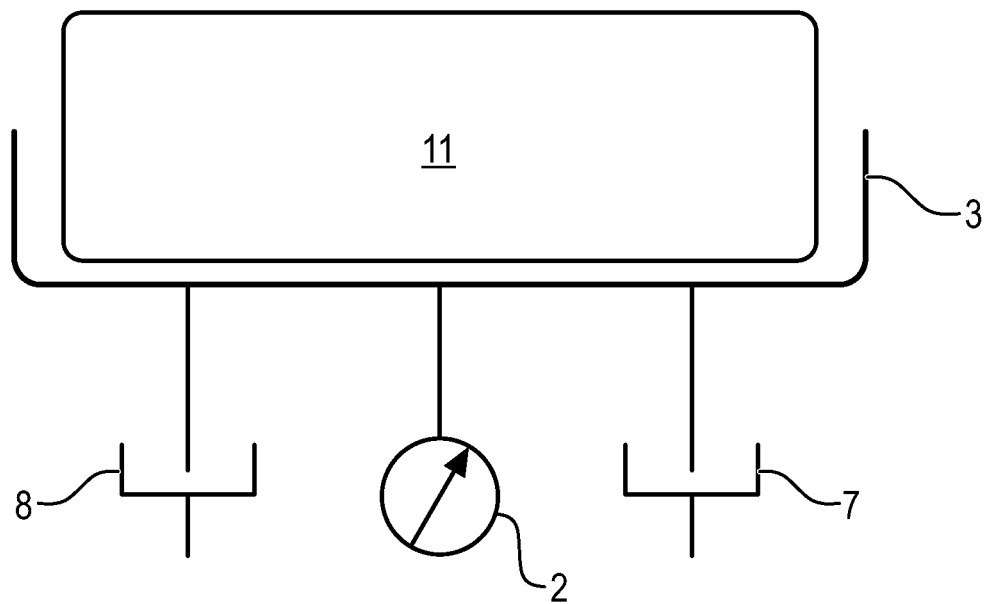

FIG. 10: a partial view of a machine to illustrate a further partial aspect.

FIG. 1 schematically shows an apparatus 1 in accordance with the invention that is configured as a gravimetric peritoneal dialysis machine for carrying out an automated point-of-care peritoneal dialysis.

The machine 1 comprises a scale 2 having a scale pan 3, a liquid storage unit 4 having a reverse osmosis filter for preparing sterile water, and a control unit not shown in the Figure. The machine 1 furthermore has a filling clamp 5 and a patient clamp 6.

A plurality of filling clamps can also be present to fill a plurality of bags of different concentrations.

At least one disposable 10 is inserted into the machine and comprises one or more solution bags 11 as well as a filling line 12 and a patient line 13. The inserted solution bag 11 is located in the scale pan 3; the filling line 12 runs through the filling clamp 5, and the patient line 13 runs through the patient clamp 6. The filling line 12 is connected to the storage unit 4. The patient line 13 is connected to a catheter of a patient.

The disposable is shown in more detail in FIG. 2. A liquid dialysis liquid concentrate is received in the bag 11 and has to be diluted by a defined quantity of sterile water to obtain a finished peritoneal dialysis solution. So that the concentrate cannot flow out into the machine before the insertion of the disposable 10, weld seams, not shown in the Figure, are provided at the bag 11 that can be opened by the user after the insertion.

As stated, a weld seam can also be opened, a cover unscrewed and a cone broken. All conceivable methods for mixing are covered by the invention.

After the insertion of the disposable 10 and the activation of the apparatus 1, the control unit first polls the weight of the bag 11 filled with concentrate determined using the scale 11 before dilution with water. The desired weight of this bag is known and is stored in or transmitted to the control unit. A check is made whether the measured weight coincides with the desired value or is within a tolerance range around the desired weight. If this check has a positive outcome, a field appears on a touch screen of the user interface, not shown in the Figure, of the machine 1 and can be actuated to start the bag filling. A visual and/or acoustic indication can also be given. If this check has a negative outcome, whether due to an incorrect or defective disposable or due to an incorrect insertion, a start of the bag filling is not released and a warning indication and a prompt to check the disposable rather appear on the screen and a warning signal can be heard. This step is shown in the time progression of FIG. 3 as a first stage between the times t0 (insertion of the bag) and t1 (start of the filling procedure).

At the time t1 shown in FIG. 3, the user starts the bag filling at the inserted disposable 10 by actuating the released activation field on the user interface of the machine 1 or by actuating a switch or by a manual opening of a clamp. The control unit thereupon closes the previously open patient clamp 6 and activates the storage unit 4 with a still open filling clamp 5. A gravimetric filling procedure or a filling procedure effected by a pump is thus started that is between the times t1 and t2 shown in FIG. 3. Sterile water slowly moves through the filling line 12 into the bag 11 during this filling procedure (time duration from t1 to t2) that can, for example, extend over a time period of approximately three hours. In this respect, the concentrate located in the bag 11 is continuously diluted and the bag weight increases linearly, as can be recognized in FIG. 3. From t2 onward, a heating unit, not shown in the Figure, of the machine 1 is activated to control the temperature of the bag 11 and of the bag contents. The preheating and the check whether the bag weight is correct take place between t2 and t3. The increase in the bag weight measured with the scale 2 during the filling procedure is continuously monitored by the control unit.

The initial drain of the patient takes place from t3 onward and the filling of the patient with fresh dialysis takes place from t4 onward (up to t5).

In the history chart in accordance with FIG. 4, two possible errors are shown that can be recognized by continuous monitoring of the bag weight during the filling procedure. A first line 31 shows the normal progression also recognizable in FIG. 3. A second line 32 shows a stagnation of the weight increase of the bag 11, which can, for example, be due to a kink or a sagging of the filling line 12. A third line 33 shows a weight reduction of the bag 11, which can, for example, be due to an unwanted backflow or due to a leak of the bag 11 or due to an incorrectly opened patient clamp. If a malfunction is recognized as in the case of the second or third line, the filling clamp 5 is immediately closed and an error message is output at the user interface of the machine 1.

At the time t2 of FIG. 3, the storage unit 4 is switched off and the filling clamp 5 is closed since a flow sensor, not shown in any more detail, and/or the scale in the storage unit 4 outputs/output a signal that the bag 11 should theoretically have to be completely filled. The control unit now starts a check procedure and measures with the scale 2 whether the filled bag 11 has reached an end weight that is known and is stored in the control unit. A check is made whether the measured weight coincides with the stored end weight or is within a tolerance range around the stored end weight. If this test has a positive outcome, the control unit, or directly the scale of the machine 1, automatically starts a dialysis treatment at the predefined time t3 by opening a drain clamp (not shown).

If this test has a negative outcome, the start of the dialysis treatment is not released and different measures can be taken such as a rectification or a warning to the user.

The dialysis treatment starts at t3 with an initial drain of consumed dialyzate from the patient. During this initial drain, the weight measured by the scale 2 increases since a section of a further disposable not shown in the Figure for consumed dialyzate coming from the patient likewise runs over the scale. The drain can thus also be monitored gravimetrically for a smooth outflow using the apparatus in accordance with the invention. At the end of the initial drain at the time t4, the patient clamp 6 is opened and the dialysis fluid flows, with a closed filling clamp 5, gravimetrically into the abdominal cavity of the patient until t5 is reached.

Figure 5A:
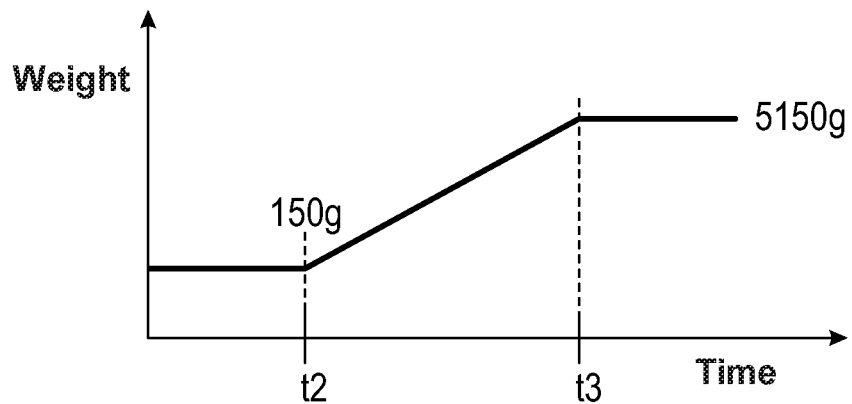
Figure 5B:
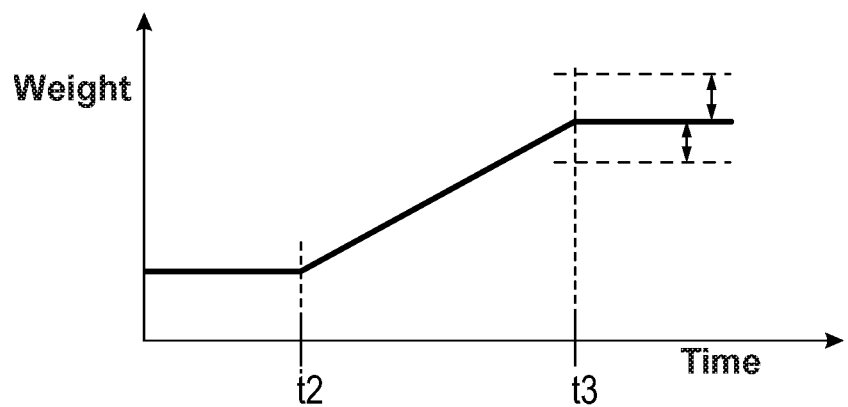
Figure 5C:
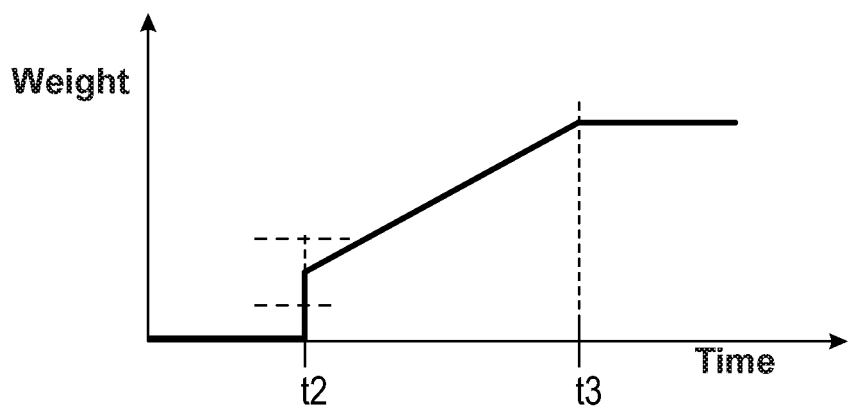

FIGS. 5a to 5c show further history charts to illustrate specific aspects of the invention.

FIG. 5a illustrates the weight progression of the bag with a linear filling with water. The scale 2 measures the weight of the bag before and after the filling (here: 150 g to 5150 g). It can be verified in this manner that the correct quantity of water was supplied to the liquid bag 11.

FIG. 5b illustrates that a desired region (here: known desired value+/−1% or also absolute values) is provided within which the weight of the filled bag should be. The desired range is defined on the basis of the permitted tolerance of the finished solution. If the weight of the filled bag 11 is outside the desired range, it is not released for the therapy.

There is also a desired range for the weight of the bag only containing the concentrate but not yet filled with water, as is illustrated in FIG. 5c. On the insertion of the disposable 10 or on the placing of the bag 11 into the scale pan 3 and consequently before the start of the dilution procedure, the weight of the bag is polled by the control unit and is checked for coincidence with the desired range. If the weight of the empty bag 11 is outside the desired range, it is not released for the filling procedure or it is diluted with correspondingly more or less liquid.

Figure 6A:
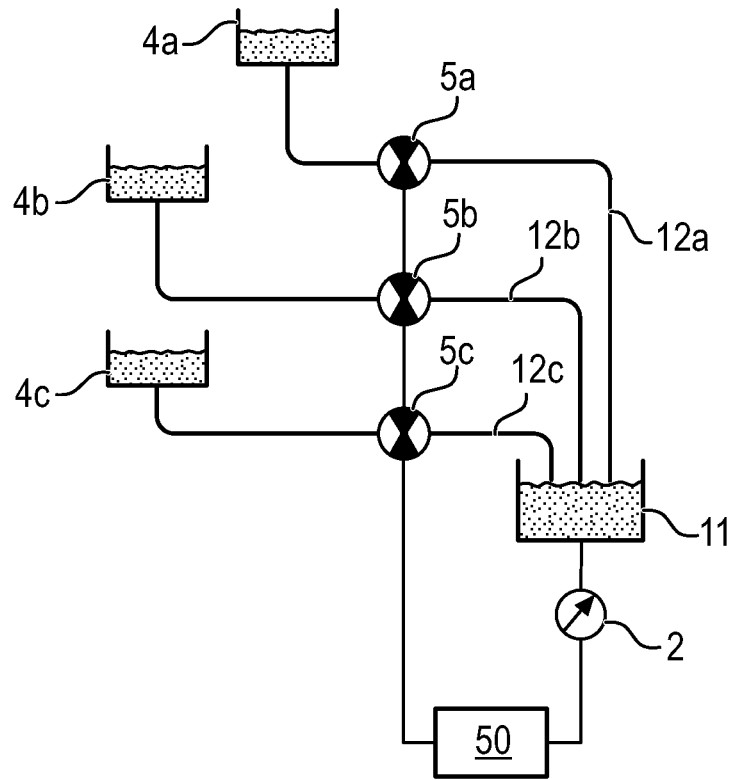
Figure 6B:
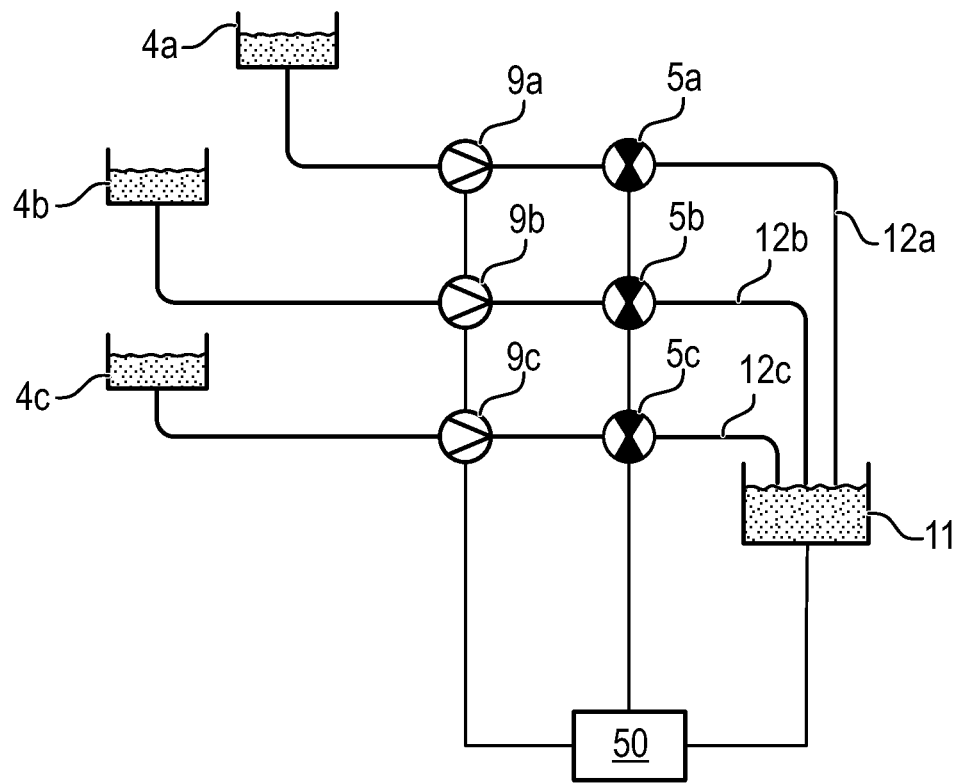

FIGS. 6a and 6b show details from the fluid schematics of a second and third embodiment of a dialysis machine of the invention. The basic design of the dialysis machine 1 is similar to the basic design of the machine 1 described in FIGS. 1 to 5. Only the means for filling the bag are designed differently. In both of these embodiments, the storage unit comprises a plurality of reservoirs 4a, 4b, and 4c for different prediluted solution components. A plurality of filling lines 12a, 12b, and 12c are furthermore provided at the disposable 10 and communicate with the individual reservoirs 4a, 4b, and 4c. The machine 1 correspondingly also comprises a plurality of clamps 5a, 5b, and 5c for the different filling lines 4a, 4b, and 4c. The bag 1 is initially not filled with a concentrate, but empty. The control unit is marked by reference numeral 50 and is inter alia connected to the clamps 5a-c and to the pumps 9a-c and/or to the scale 2.

In the second embodiment in accordance with FIG. 6, the control unit 50 is configured to regulate the liquid quantity filled into the solution bag 11, that is the opening and closing of the clamps 5a-5c with reference to the signal of the scale 2.

Only the signal of the scale 2 is used by the control unit 50 to regulate the flow to the solution bag 11. A balancing pump and a flow sensor are not provided.

In the third embodiment in accordance with FIG. 6b, the control unit 50 is configured to control the liquid quantity filled into the solution bag 11 using the balancing pumps 9a-9c in addition to the clamps 5a-5c and only to make use of the signal of the scale 2 to check the liquid quantity filled into the solution bag 11.

FIG. 7 shows the history chart for the bag weight in the second and third embodiments of the invention. In both of these embodiments, the control unit is configured to initiate a sequential filling of the solution bag 11 with the different solution components, namely either gravimetrically using the clamps 5a-5c (second embodiment in accordance with FIG. 6a) or actively using the pumps 9a-9c and clamps 5a-5c (third embodiment in accordance with FIG. 6b). A filling step with a concentrate containing an osmotic agent (here: glucose) from reservoir 4a that ends at the time t1, is started at the time to. At the time t2, a filling step with an electrolyte and buffer concentrate from reservoir 4b is started that ends at the time t3. At the time t4, a filling step with water from reservoir 4c is started that ends at the time t5.

Figure 8A:
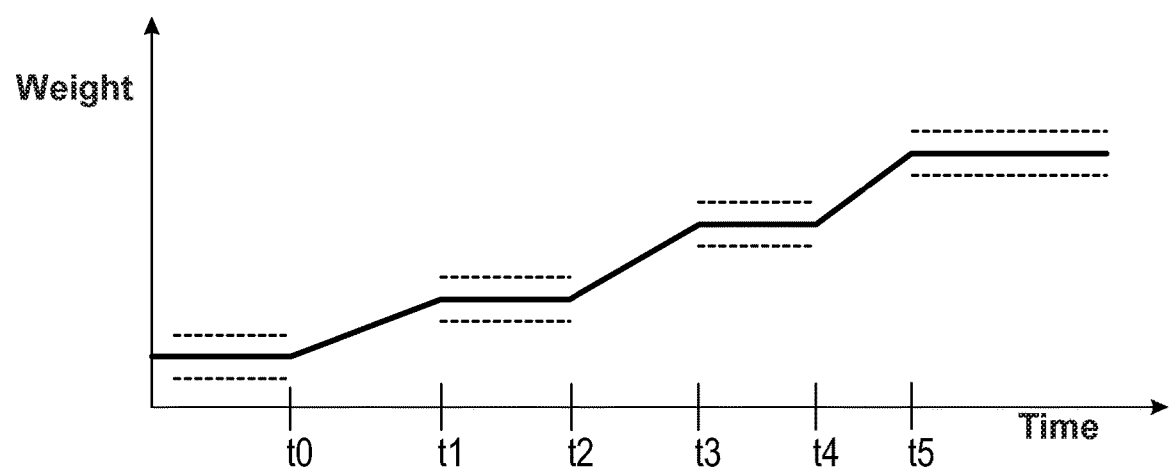

Provision is made in the third embodiment in accordance with FIG. 6b that the control unit 50 verifies the weight of the solution bag using the scale 2 before the filling procedure and after every step of the sequential filling procedure as to whether a correct liquid quantity has flowed into the solution bag 11. Desired ranges are also provided for every measurement here, as is illustrated in FIG. 8a. If the weight of the bag 11 is outside the desired range, it is not released for the next step by the control unit 50 in a manner such as has already been described in another connection.

Figure 8B:
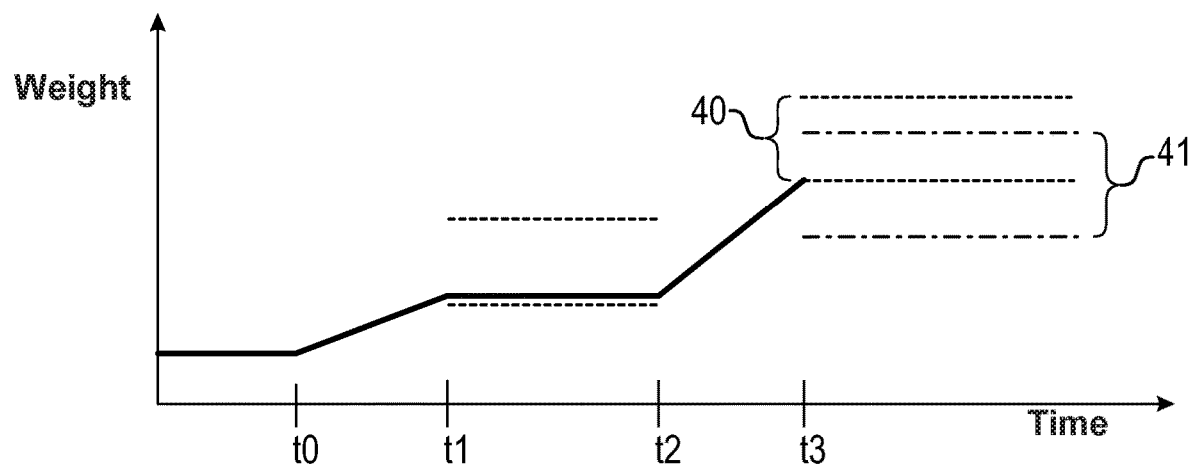

The limits of the respective desired ranges are not rigidly defined in this embodiment, but are rather individually determined by the addition of fixed amounts to the actual weight of the bag 11 determined in the preceding step. It can thus be avoided that the weight verification is falsified by an amount of an earlier deviation from the desired value. This is illustrated in FIG. 8b. A scenario is reproduced there in which the bag weight after the time t1 is within the desired range, but not exactly at the desired value, but rather close to the lower end of the desired region. Reference symbol 40 now designates the uncorrected desired range for the bag weight after the time 63 that would apply under the condition, not satisfied here, that the bag weight in the preceding step, i.e. after the time t1, would exactly correspond to the desired value. Reference numeral 41 designates the corrected desired value that is oriented on a corrected desired value for the bag weight after the time t3 that is obtained by addition of a desired difference to the actual bag weight in the preceding step, that is between the times t1 and t2.

Figure 9A:
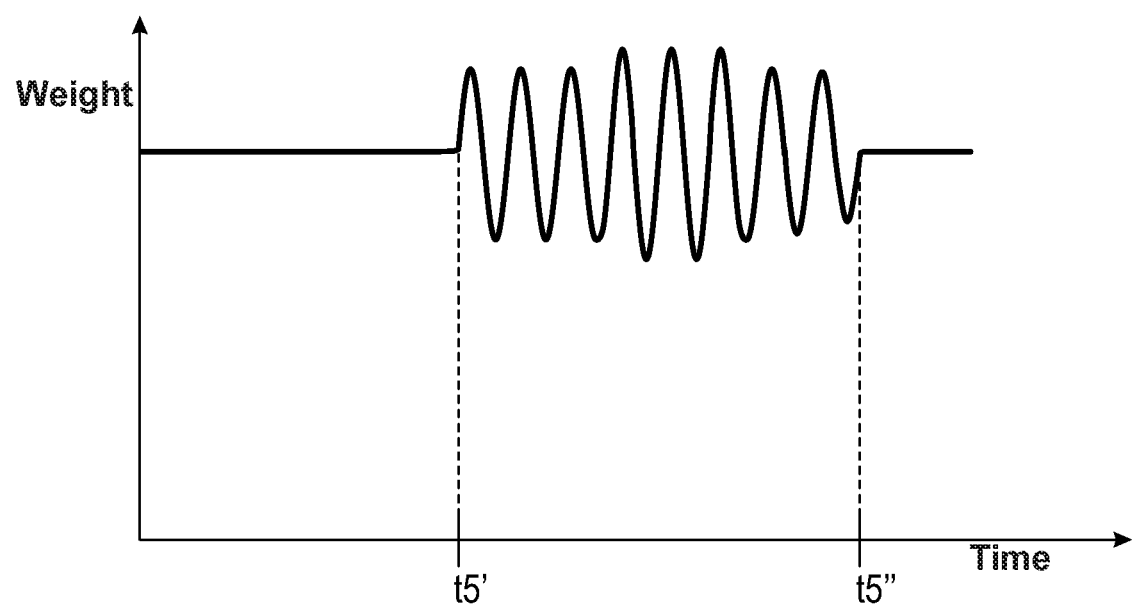
Figure 9B:
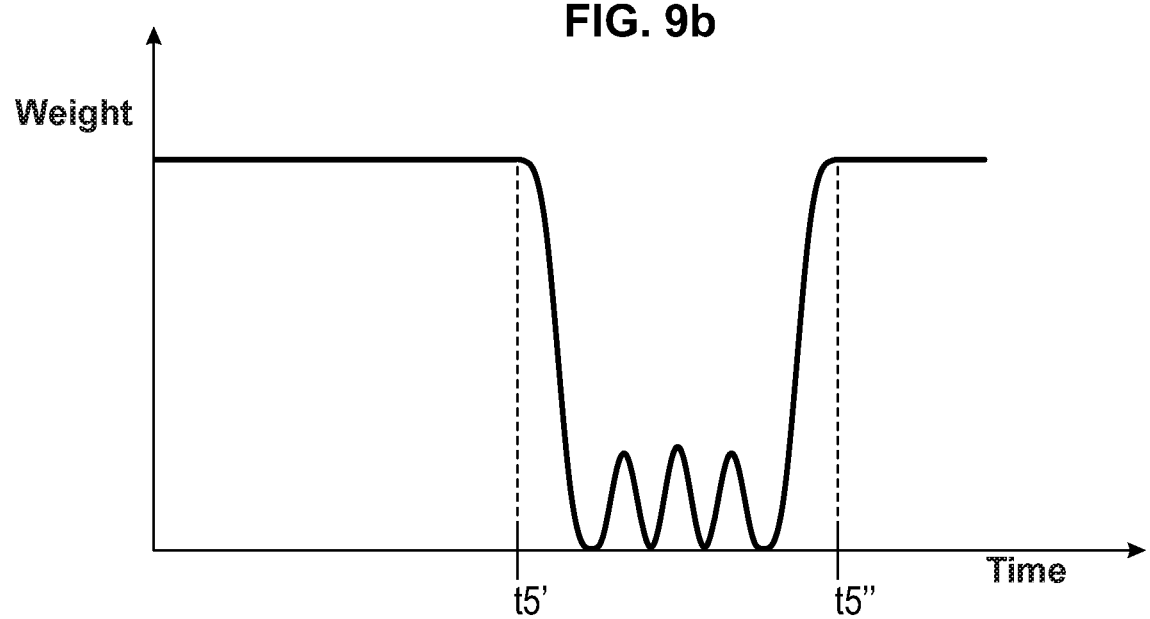

FIGS. 9a and 9b shows enlarged views of the history chart for the second embodiment after the time t5, that is after the solution bag 11 has been filled with all three partial solutions and the filling procedure has ended. It can be recognized that a signal change occurs in both cases between the times t5' and t5". This disturbance is representative for a shaking of the bag 11 disposed in the scale pan 3 (FIG. 9a) or for a brief removal of the filled bag 11 from the scale pan 3 (FIG. 9b).

These disturbances result from the fact that the control unit in the respective embodiments is configured to output a signal after the end of the filling procedure to request a movement of the filled solution bag 11. The user should thus be caused to move the solution bag 11 for the homogeneous mixing of the solution components after its complete filling. The control unit 50 can then verify with reference to the scale 2 whether such a movement has actually been carried out, namely with reference to a recognition of the interference images shown in FIGS. 9a and 9b respectively. If no such interference image is recognized after the request, the filled bag 11 is not released for the therapy.

FIG. 10 shows a modified variant with two actuators 7 and 8 for shaking the scale pan 3. In this embodiment, the scale 3 and consequently the solution bag 11 arranged therein can be automatically shaken by the machine after the end of the filling procedure without the user having to be prompted to do so or having to carry it out.

The invention claimed is:

1. A gravimetric apparatus for preparing a peritoneal dialysis solution at the point of use, comprising:

a disposable having a solution bag and associated filling line and patient line;
a storage unit for liquid connected to the filling line;
a control unit; and
a flow regulator for regulating a flow from the storage unit to the disposable, wherein
the gravimetric apparatus further comprises a scale at which the solution bag of the disposable is arranged,
the control unit is configured to (i) initiate, by gravimetric flow using the flow regulator, a filling of the solution bag with liquid from the storage unit using the actuators, and to determine the quantity of the liquid that has flowed into the solution bag using the scale, (ii) stop the filling procedure after reaching a predefined filling quantity and to verify, by use of the scale, whether the weight of the bag is within a desired range after the stopping of the filling procedure, and (iii) fix the limits of the desired range by addition of a specific amount to the determined starting weight of the bag or to a weight of the bag determined after the preceding step,
the gravimetric apparatus is a dialysis machine,
the gravimetric apparatus has a filling clamp and a patient clamp,
the filling line of the disposable is inserted into the filling clamp,
the patient line is inserted into the patient clamp,
the control unit is configured to carry out the filling of the solution bag with an open filling clamp and a closed patient clamp,
the gravimetric apparatus has a further disposable or the disposable has an additional cavity for dialyzate flowing out of the patient,
the further disposable or additional cavity is arranged on the same scale as the solution bag, and
the control unit is configured to gravimetrically determine the quantity of the dialyzate flowing off from the patient as part of a dialysis treatment.

2. An apparatus in accordance with claim 1, wherein the control unit is configured to regulate the liquid quantity filled into the solution bag using the signal of the scale.

3. An apparatus in accordance with claim 1, wherein: the solution bag is pre-filled with a dialysis fluid concentrate; that the storage unit is a water preparation unit; and in that the liquid filled into the solution bag is water.

4. An apparatus in accordance with claim 3, further comprising a check valve, wherein the check valve is arranged in the filling line and suppresses a flow from the bag to the water preparation unit.

5. An apparatus in accordance with claim 1, wherein: the storage unit is configured to provide at least two different fluid solution components; and in that the control unit is configured to initiate a sequential filling of the solution bag with the different solution components.

6. An apparatus in accordance with claim 1, wherein the control unit is configured to output a signal and/or to suppress a start of the filling procedure when the starting weight of the bag, determined using the scale, falls below or exceeds a threshold value.

7. An apparatus in accordance with claim 1, wherein the control unit is configured to output a signal, after the end of the filling procedure, to request a movement of the filled solution bag and to verify, by means of the scale, whether the solution bag has actually been moved.

8. An apparatus in accordance with claim 1, wherein the apparatus has an actuator that is configured to be able to move the inserted solution bag, and that the control unit is configured to move the solution bag after the end of the filling procedure.

9. An apparatus in accordance with claim 1, wherein the control unit is configured to output a signal and/or to stop the pump of the storage unit and/or to close a filling clamp if a stagnation of the weight increase or a weight reduction of the solution bag is recognized with reference to the scale during the filling procedure.

10. An apparatus in accordance with claim 1, wherein the apparatus has a heating device and the control unit is configured to heat the bag during the filling procedure or after the filling procedure.

11. An apparatus in accordance with claim 1, wherein the apparatus has a graphical user interface having a touch screen, and the control unit is configured to visualize the progression of the filling procedure at the user interface and/or to output signals.

\* \* \* \* \*